*(12)* United States Patent
Ajani et al.

(10) Patent No.: US 8,143,240 B2
(45) Date of Patent: Mar. 27, 2012

(54) 17α, 21-DIHYDROXYPREGNENE ESTERS AS ANTIANDROGENIC AGENTS

(75) Inventors: Mauro Ajani, Lainate (IT); Luigi Moro, Cairate (IT)

(73) Assignee: Cosmo S.p.A., Lainate (Milan) (IT)

( * ) Notice: Subject to any disclaimer, the term of this patent is extended or adjusted under 35 U.S.C. 154(b) by 172 days.

(21) Appl. No.: 12/457,870

(22) Filed: Jun. 24, 2009

(65) Prior Publication Data

US 2009/0264396 A1    Oct. 22, 2009

Related U.S. Application Data

(62) Division of application No. 10/486,386, filed on Sep. 16, 2004, now abandoned.

(30) Foreign Application Priority Data

Aug. 10, 2001  (IT) .............................. MI2001A1762

(51) Int. Cl.
*A61K 31/56*    (2006.01)
(52) U.S. Cl. ....................................... 514/178; 514/179
(58) Field of Classification Search .................. 514/178, 514/179
See application file for complete search history.

(56) References Cited

U.S. PATENT DOCUMENTS

| | | | | |
|---|---|---|---|---|
| 2,985,650 | A | 5/1961 | Batres et al. | |
| 3,152,154 | A | 10/1964 | Gardi et al. | ................... 552/566 |
| 4,670,427 | A | 6/1987 | Annen et al. | |
| 5,264,428 | A | 11/1993 | Streber | ......................... 514/177 |

FOREIGN PATENT DOCUMENTS

| | | |
|---|---|---|
| EP | 791771 | 2/1958 |
| JP | 59-106500 | 6/1984 |
| JP | 60-161998 | 8/1985 |

OTHER PUBLICATIONS

BeLieu (Obstetrics and Gynecology Clinics of North America (1994) 21:461-477).*
Meriggiola et. al. (Expert Opinion on Investigational Drugs (2006) 15:389-397).*
Biollaz, M. et al; "Reaktionen von Steroiden mit Dialkylaminoschwefeltrifluoriden"; *Helvetica Chimica ACTA*; vol. 60, No. 8, 1077, pp. 2703-2710; XP009000425 (compound 2).
Annen, K. et al; "17-Pivalate in der Pregnanreihe"; *Liebigs Ann. Chem.*; 1983, pp. 705-711, XP001119196 (compound 5b).
Biollaz et al; Helvetica Chimica Acta, vol. 60(8), pp. 2703-2710 (1977).
Morrison and Boyd, 6th Edition, pp. 764-765 (1992).

* cited by examiner

*Primary Examiner* — Marcos Sznaidman
(74) *Attorney, Agent, or Firm* — Nixon & Vanderhye

(57) ABSTRACT

17α,21-Dihydroxypregna-4,9-diene-3,20-dione and 17α,21-dihydroxypregna-4-ene-3,20-dione 17 and/or 21 esters of having remarkable antiandrogenic activity, and the processes for the preparation thereof.

9 Claims, No Drawings

17α, 21-DIHYDROXYPREGNENE ESTERS AS ANTIANDROGENIC AGENTS

This application is a divisional of application Ser. No. 10/486,386, filed Sep. 16, 2004 now abandoned, the entire content of which is hereby incorporated by reference in this application.

The present invention relates to 17α,21-dihydroxypregnene esters, processes for the preparation thereof and the use thereof as antiandrogenic agents.

PRIOR ART

A number of corticosteroids have been used as anti-inflammatory, anti-rheumatic, anti-allergic and anti-shock agents.

In particular, 11-deoxy-hydrocortisone esters and derivatives thereof have been widely used as anti-inflammatories.

No 17α,21-dihydroxypregnene mixed esters are known, while 17 and 21 acyl derivatives with equal aliphatic chains having no more than four carbon atoms have been described.

Carboxylic acids 17 or 21 monoesters having no more than six carbon atoms are also known.

For example, the preparation of 17α,21-diacetoxypregna-4-ene-3,20-dione is disclosed in U.S. Pat. No. 3,530,038, that also mentions the use of propionyl derivatives and a series of aliphatic acyl derivatives having up to six carbon atoms chains.

U.S. Pat. No. 3,152,154 discloses the preparation of 21-hydroxypregna-4,9-diene-3,20-dione-17α-butyrate, which is used as an intermediate for the preparation of 3,21-diacyloxy-17α-butanoyloxypregna-3,5,9-triene-20-one wherein the 3 and 21 acyls are the same and are acetyl, propanoyl, butanoyl and isobutanoyl. All of the examples cited in these documents concern compounds wherein the 17α and 21 positions are esterified with the same acyl group.

The preparation of 21-acetoxypregna-4-ene-3,20-dione-17α-dimethyl propionate is described in Liebigs Ann. Chem. 1983, 705-711 as the only example of mixed esters: the Authors state that the preparation of the mixed ester is possible only when the substituent in position 21 is an acetyl.

U.S. Pat. No. 3,530,038 discloses a process for the preparation of 11β-17α-21-trihydroxy steroids which comprises subjecting 11-deoxy-17α-OR-21-OR' steroids, wherein R is a carboxylic acid residue of 1-18 carbon atoms and R' is hydrogen or an acyl of 1 to 18 carbon atoms, to microbiological oxidation with Curvularia for obtaining the corresponding 11β-hydroxy steroid.

According to the same patent, compounds of the pregnane, androstane or estrane series are mentioned as possible starting steroids, but no mention is made of any transformation of 11-deoxy-17α-OR-21-OR' steroids wherein R is an acyl of 1-18 carbon atoms and R' is hydrogen.

The preparation of these products was described by R. B. Turner (J. Am. Chem. Soc. 75 (1953) 3489) with reference to the preparation of pregna-4-ene-3,20-dione-17α,21-diacetate and by R. Gardi et al. (Gazz. Chim. It. 93 (1963) 431-450).

Finally, U.S. Pat. No. 3,780,177 discloses the preparation of 21-hydroxy-pregna-4,9-diene-3,20-dione-17α-butanoate by means of orthobutyrates and the use thereof as an intermediate for the preparation of 6α,9α-difluoroprednisolone 17-butanoate-21 ester derivatives.

SUMMARY OF THE INVENTION

It has now been found that some 17α,21-dihydroxypregna-4,9-diene-3,20-dione and 17α,21-dihydroxypregna-4-ene-3,20-dione 17 and/or 21 esters have remarkable antiandrogenic activity.

Therefore, according to a first embodiment, the present invention relates to compounds of formula (I)

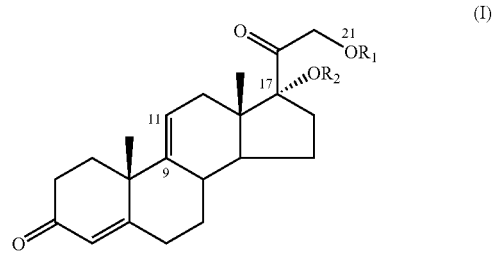

(I)

wherein:

$R_1$ and $R_2$, which can be the same or different, are hydrogen or a $C_3$-$C_{18}$ acyl group, with the provisos that:
  at least one of $R_1$ and $R_2$ is different from hydrogen;
  when $R_1$ is hydrogen, $R_2$ is different from butyroyl.

According to a second embodiment, the invention relates to compounds of formula (II)

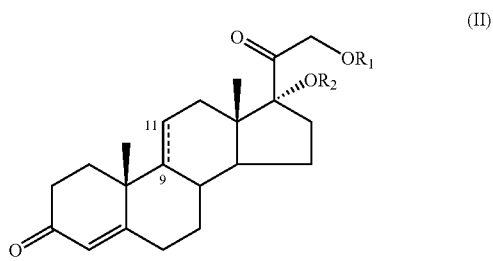

(II)

wherein:

$R_1$ and $R_2$, which can be the same or different, are hydrogen or a $C_3$-$C_{18}$ acyl group, with the proviso that:
  at least one of $R_1$ and $R_2$ is different from hydrogen; as antiandrogenic drugs.

According to a further embodiment, the invention relates to a process for the preparation of compounds of formula (I) or (II) in which $R_1$ and $R_2$ are both acyl, groups, which process, comprises reacting the corresponding compounds, wherein $R_1$ and $R_2$ are hydrogen, with carboxylic acids anhydrides or active esters in inert solvents and at temperatures ranging from −5° C. to the reaction mixture boiling temperature.

Still a further object of the invention relates to a process for the preparation of compounds of formula (I) or (II) wherein one of $R_1$ or $R_2$ is hydrogen and the other is acyl, which process comprises:

a. reaction of the corresponding compounds wherein $R_1$ and $R_2$ are hydrogen with $C_3$-$C_{18}$ carboxylic acids anhydrides or active esters or with allyloxycarbonyl chloride or isobutene in inert solvents and at temperatures ranging from −5° C. to the boiling temperature, for obtaining the corresponding compound in which $R_1$ is isobutyl, allyloxycarbonyl or $C_3$-$C_{18}$ acyl;

b. optional reaction of the compound from step a) with $C_3$-$C_{18}$ carboxylic acids anhydrides or active esters in inert solvents and at temperatures ranging from −5° C. to the reaction mixture boiling temperature;

c. optional lysis of the 21-allyloxycarbonyl or 21-isobutyloxy group.

Finally, the invention relates to pharmaceutical compositions with antiandrogenic activity containing as active ingredient the compounds of formula (I) or (II).

DETAILED DISCLOSURE OF THE INVENTION

Preferred compounds of formula (I) are:
17α,21-dibutanoyl-pregna-4,9-diene-3,20-dione;
17α-hydroxy-21-butanoyl-pregna-4,9-diene-3,20-dione;
17α-hydroxy-21-butanoyl-pregna-49-di-ene-3,20-dione;
17α-butanoyl-2-octadecanoyl-pregna-4,9-diene-3,20-dione;
17α-octadecanoyl-21-butanoyl-pregna-4,9-diene-3,20-dione.

The antiandrogenic activity of the compounds of formula (I) and (II) has been evaluated in the animal according to the conventional test for the topical antiandrogenic activity described by W. Voigt and S. L. Hsia (Endocrinology 1973; 92: 1216-1222).

The test was carried out on sexually immature female hamsters aged 6-8 weeks and weighing 65-90 grams.

At the beginning of the tests, the back of each animal was shaved to evidence the respective flank organ bilaterally. Animals were then subdivided into homogeneous groups and treated daily for 21 consecutive days. The tested steroids were dissolved at concentrations ranging from 100 to 400 micrograms in 50 microliters of an acetone solution containing 4 micrograms of testosterone propionate (TP) or 4 micrograms of dihydrotestosterone (DHT). 50 microliters of the solutions were applied to the right flank organ, while the contralateral organ used as individual control received only acetone (50 microliters). Control groups received TP or DHT alone, following the same procedures.

At the end of the tests, the animals were killed under ether anesthesia and the whole skine of the back was taken. The area of both flank organs was measured, separately, with transillumination. The mean differences between areas treated with the tested steroids and those treated with the carrier alone were calculated for each group, and said mean differences were compared, as inhibition percentages, to the mean differences between the areas in the control groups treated with either TP or DHT.

By way of example, in the topical antiandrogenic activity test 17α-propionyl-21-hydroxy-pregna-4,9-diene-3,20-dione, and the corresponding 17α,21-dibutyrate and 17α-butyrate inhibited by more than 80% the androgenic action of testosterone propionate (TP) and by 50 to 80% the action of its active derivative dihydrotestosterone (DHT).

The compounds of the invention proved active at doses ranging from 10 to 4000 micrograms.

The compounds of the invention can be used as suitable pharmaceutical compositions for the topical and/or systemic treatment, through the oral, cutaneous or mucosal route, of conditions such as: acne, seborrhea, hirsutism, alopecia, mastodynia, prostate hyperplasia and carcinoma, virilization syndromes in the female, early puberty, inhibition of sexual aggressiveness in the male, contraception in the male.

According to the process of the invention, compounds of formula (I) or (II) wherein $R_1$ and $R_2$ are both acyl groups are prepared by esterification of 17α,21-dihydroxypregna-4-ene-3,20-dione or 17α,21-dihydroxypregna-4,9-diene-3,20-dione hydroxy groups with active esters containing the desired acyl group. According to this simple procedure, acyl derivatives with hindering aliphatic chains, such as those with high number of carbon atoms or branched, can be prepared. Examples of suitable active esters for this reaction are trifluoroethyl butyrate or trifluoroethyl octadecanoate, which can both attain excellent esterification yields with the aid of a lipase in inert anhydrous solvents at temperatures ranging from 20 to 50° C. and with reaction times ranging from 20 to 100 hours. Examples of lipases are PPL (porcine pancreatic lipase) or those from *Candida cylindracea*.

The process for the preparation of the compounds of formula (I) or (II) wherein one of $R_1$ o $R_2$ is hydrogen and the other is acyl comprises the following steps:

1. The 21 hydroxyl is selectively esterified with allyloxycarbonyl chloride, benzyloxy carbonyl chloride, tert-butylcarbonyl chloride in dimethylformamide or isobutene at temperatures from −5 to 40° C.

2. The resulting 21 monoester is then subjected to esterification with anhydrides of carboxylic acids of 7 carbon atoms in the presence of 4-dimethylaminopyridine as catalyst. Alternative to the esterification in 17 is the use of the carboxylic acid in the presence of dicyclohexylcarbodiimide. Active esters such as trifluoroethyl derivatives or N-acylphthalimide or N-acylbenzotriazoles are further alternatives.

3. The protection in 21 is removed with, for example, tetrakis(triphenylphosphine) Pd and triphenyl phosphine in dichloromethane or tetrahydrofuran to obtain 17α-acyl-21-hydroxypregna-4-ene-3,20-dione or 17α-acyl-21-hydroxypregna-4,9-diene-3,20-dione.

4. The product from step 3) can subsequently be esterified in 21 with anhydrides of carboxylic acids of 7 carbon atoms or alternatively with the carboxylic acid in the presence of dicyclohexylcarbodiimide, or with active esters such as trifluoroethyl derivatives or N-acylphthalimides or N-acylbenzotriazoles.

Example 1

Preparation of
17α,21-dibutanoyl-pregna-4,9-diene-3,20-dione

A mixture of 1 g (2.87 mM) of 17α,21-dihydroxy-pregna-4,9-diene-3,20-dione and of 10 ml of trifluoroethyl butanoate in 50 ml of tetrahydrofuran was reacted at 45° C. in the presence of 5 g of *Candida cylindracea* lipase for 8-10 hours, adding 1 g of lipase at regular time intervals. At the end of this first reaction step, the lipase was filtered off and the filtrate was concentrated under vacuum taking up the residue three times with tetrahydrofuran. The resulting residue was added with further 10 ml of trifluoroethyl butanoate and 50 ml of tetrahydrofuran, the resulting solution was added with 0.8 g of *Bacillus subtilis* protease and the suspension was stirred for 2 days at 45° C., adding further protease at regular time intervals for total 80 mg. The protease was filtered off, the filtrate was removed under vacuum and the residue was chromatographed on a silica gel column with a dichloromethane/methanol 99:1 mixture. The less polar fraction was evaporated to obtain 1 g (2.06 mM) of 17α,21-dibutanoyl-pregna-4,9-diene-3,20-dione.

The same procedure was followed, starting from 1 g of 17α,21-dihydroxy-pregna-4-ene-3,20-dione, to obtain 0.98 g (2.01 mM) of 17α,21-dibutanoyl-pregna-4-ene-3,20-dione.

Example 2

Preparation of 17α-hydroxy-21-butanoyl-pregna-4,9-diene-3,20-dione

A mixture of 1 g (2.879 mM) of 17α,21-dihydroxy-pregna-4,9-diene-3,20-dione and 10 ml of trifluoroethyl butanoate in 100 ml of acetone was reacted at 45° C. in the presence of 5 g of *Candida cylindracea* lipase for 8-10 hours, adding 1 g of lipase at regular time intervals. After completion of the reaction, the lipase was filtered off and the filtrate was concentrated under vacuum, taking up the residue three times with acetone. The semi-solid residue was purified by chromatography on a silica gel column with a dichloromethane/methanol 99:1 mixture. The less polar components were removed, to obtain the richer fraction which was evaporated to yield 0.95 g (2.29 mM) of 17α-hydroxy-21-butanoyl-pregna-4,9-diene-3,20-dione.

Example 3

Preparation of 17α-hydroxy-21-butanoyl-pregna-4-ene-3,20-dione

A mixture of 1 g of 17α,21-dihydroxy-pregna-4-ene-3,20-dione and 10 ml of trifluoroethyl butanoate in 50 ml of methyl ethyl ketone was reacted at 45° C. in the presence of 5 g of *Candida cylindracea* lipase for 8-10 hours, adding at regular time intervals 1 g of lipase. After completion of the reaction, the lipase was filtered off, the filtrate was concentrated under vacuum, taking up the residue three times with solvent. The semi-solid residue was purified by chromatography on a silica gel column with a dichloromethane/methanol 99:1 mixture. The richer fraction was evaporated to obtain 0.89 g (2.14 mM) of 17α-hydroxy-21-butanoyl-pregna-4-ene-3,20-dione.

Example 4

Preparation of 17α-butanoyl-21-octadecanoyl-pregna-4,9-diene-3,20-dione 4 g (11.6 mM) of 17α,21-dihydroxy-pregna-4,9-diene-3,20-dione were reacted with 20 mg of trifluoroacetic acid in 20 ml of dioxane and 10 ml of ethyl orthobutyrate for 5 hours at 100° C., and the low boiling head fraction was distilled off. The solution was cooled, then treated with 5 ml of a tartaric acid molar solution and heated to 40-50° C. for about 5 minutes to obtain 17α-butanoyl-21-hydroxy-pregna-4,9-diene-3,20-dione. The solvent was evaporated off under vacuum and the residue was repeatedly taken up with dioxane. The resulting residue was dissolved in 200 ml of acetone and then 12 g trifluoroethyl octadecanoate (prepared from octadecanoyl chloride and trifluoroethanol), 20 g of *Candida cylindracea* lipase were added and the resulting suspension was stirred for 8-10 hours at 50° C., adding 2 g of *C. cylindracea* at regular time intervals. The lipase was filtered off, the filtrate was concentrated under vacuum and the residue was chromatographed on a silica gel column with a dichloromethane/methanol 98.5:1.5 mixture. The neat fraction was evaporated to obtain 4.9 g (7.17 mM) of 17α-butanoyl-21-octadecanoyl-pregna-4,9-diene-3,20-dione.

The same procedure was followed, starting from 5 g (14.5 mM) of 17α,21-dihydroxy-pregna-4-ene-3,20-dione, to obtain 5.9 g (8.61 mM) of 17α-butanoyl-21-octadecanoyl-pregna-4-ene-3,20-dione.

Example 5

Preparation of 17α-octadecanoyl-21-butanoyl-pregna-4,9-diene-3,20-dione

Step a: A solution of 2 g of NaOH in 20 ml of water was added with 25 ml of tetrahydrofuran and 5 g (14.5 mM) of 17α,21-dihydroxy-pregna-4,9-diene-3,20-dione. The mixture was stirred at 0° C., then 2.4 ml of allyl chloroformate was dropwise added. After stirring for about 0.5 hours at this temperature, the mixture was carefully neutralized with hydrochloric acid and extracted with dichloromethane. The organic extract was concentrated under vacuum and the residue was subjected to the reaction of the subsequent step.

Step b: Crude 17α-hydroxy-21-allylcarbonyloxy-pregna-4,9-diene-3,20-dione was dissolved in 15 g of trifluoroethyl octadecanoate and 150 ml of tetrahydrofuran, the resulting solution was added with 4 g of *Bacillus subtilis* protease and the suspension was stirred for 2 days at 45° C., adding further protease at regular time intervals to 3 g total. The protease was filtered off, the filtrate was removed under vacuum and the residue was chromatographed on a silica gel column with a dichloromethane/methanol 99:1 mixture. The less polar fraction was evaporated off to obtain a residue of 17α-octadecanoyl-21-allylcarbonyloxy-pregna-4,9-diene-3,20-dione.

Step c: the residue from the previous step was dissolved in 50 ml of dichloromethane and added with 35 mg of triphenylphosphine and 35 mg of palladium triphenylphosphine. The resulting mixture was stirred for 0.5 hours at room temperature. The solution was concentrated under vacuum, the residue was taken up twice with dichloromethane, then chromatographed on a silica gel column with a dichloromethane/methanol 99:1 mixture. The richer fraction was evaporated to obtain a neat residue, which was used as such for the subsequent step.

Step d: the residue (6.2 g) of 17α-octadecanoyl-21-hydroxy-pregna-4-ene-3,20-dione was dissolved in 4 ml butyric anhydride in the presence of 0.5 g of tributylmethylammonium chloride. The mixture was stirred at room temperature for 2 hours, then poured in ice and the resulting product was separated from water by extraction. The extract was washed to neutrality with water and concentrated under vacuum, the residue was crystallized from methanol to obtain 5.5 g (8.05 mM) of 17α-octadecanoyl-21-butanoyl-pregna-4,9-diene-3,20-dione. This compound was used for the preparation of a pharmaceutical formulation in the form of a cream suitable for cutaneous administration.

The same procedure was followed, starting from 5 g (14.5 mM) of 17α,21-dihydroxy-pregna-4-ene-3,20-dione, to obtain 5.1 g (7.44 mM) of 17α-octadecanoyl-21-butanoyl-pregna-4-ene-3,20-dione.

The compounds of Examples 1-5 were formulated in suitable formulations, for example in the form of liposome emulsions or suspensions for the transmucosal administration to provide either systemic or topical action, creams, gel and the like.

A typical cream formulation will contain, for example, cetyl alcohol, glycerol monostearate, liquid paraffin, propylene glycol, disodium mono-oleo-amido sulfosuccinate, citric acid monohydrate, purified water.

Using substantially the same methods disclosed in the above examples, the following compounds were prepared:

17α,21-dibutanoyl-pregna-4-ene-3,20-dione (mp 101° C., isopropyl ether);

17α-propionyl-21-hydroxy-pregna-4-ene-3,20-dione (mp 114° C., isopropyl ether).

Example 6

Topical Antiandrogenic Activity of 17α-propionyl-21-hydroxy-pregna-4,9-diene-3,20-dione (Compound A)

| Topical treatment | Daily dosage (μg) | Mean difference of the areas (mm$^2$) | % inhibition |
|---|---|---|---|
| Carrier (acetone) | — | 0.0 | — |
| TP | 4 | 22.7 ± 2.3 | — |
| TP + A | 4 + 400 | 3.7 ± 1.1 | 84 |
| DHT | 4 | 20.8 ± 2.5 | — |
| DHT + A | 4 + 400 | 9.7 ± 1.8 | 53 |

Example 7

Topical Antiandrogenic Activity (Compound of Example 1)

| Topical treatment | Daily dosage (μg) | Mean difference of the areas (mm$^2$) | % inhibition |
|---|---|---|---|
| Carrier (acetone) | — | 0.0 | — |
| TP | 4 | 22.7 ± 2.3 | — |
| TP + Ex. 1 | 4 + 400 | 2.4 ± 1.1 | 89 |
| DHT | 4 | 20.8 ± 2.5 | — |
| DHT + Ex. 1 | 4 + 400 | 3.7 ± 0.7 | 82 |

Example 8

Topical Antiandrogenic Activity (Compound of Example 2)

| Topical treatment | Daily dosage (μg) | Mean difference of the areas (mm$^2$) | % inhibition |
|---|---|---|---|
| Carrier (acetone) | — | 0.0 | — |
| TP | 4 | 22.7 ± 2.3 | — |
| TP + Ex. 2 | 4 + 400 | 3.3 ± 1.2 | 85 |
| DHT | 4 | 20.8 ± 2.5 | — |
| DHT + Ex. 2 | 4 + 400 | 4.1 ± 0.5 | 80 |

The invention claimed is:

1. A method of treating a patient suffering from a condition selected from the group consisting of acne, seborrhea, hirsutism and alopecia, comprising administering to said patient topically or systemically an effective amount of a compound of formula (I)

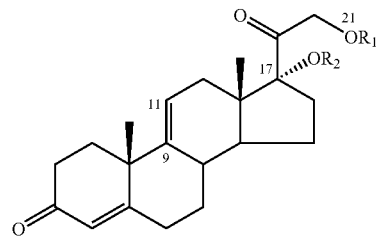

wherein:

$R_1$ is hydrogen and $R_2$ is a $C_3$-$C_{18}$ acyl group.

2. A method of treating a patient suffering from a condition selected from the group consisting of acne, seborrhea, hirsutism, and alopecia, said method comprising administering to said patient an effective amount of a compound of formula (II)

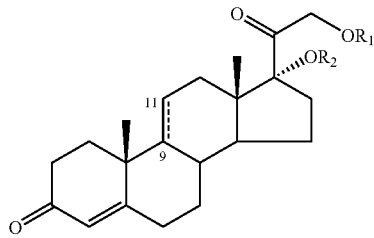

wherein:

$R_1$ and $R_2$, which can be the same or different, are hydrogen or a $C_3$-$C_{18}$ acyl group, with the proviso that at least one of $R_1$ and $R_2$ is different from hydrogen.

3. The method as claimed in claim 2 wherein $R_1$ is hydrogen and $R_2$ is propionyl.

4. The method as claimed in claim 2 wherein $R_1$ and $R_2$ are butanoyl.

5. A method of treating a patient suffering from a condition selected from the group consisting of acne, seborrhea, hirsutism and alopecia, comprising administering to said patient topically or systemically an effective amount of a pharmaceutical composition comprising as active ingredient a compound of formula (I)

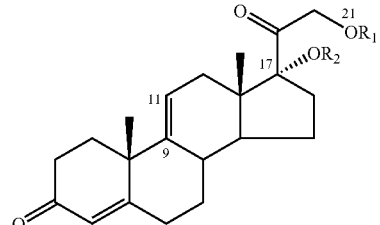

wherein:

R$_1$ is hydrogen and R$_2$ is a C$_3$-C$_{18}$ acyl group, in admixture with an acceptable carrier, wherein said active ingredient is present in an amount of 0.1 to 1.0% by weight.

6. The method as claimed in claim 2, wherein the compound of formula (II) is administered topically or systemically.

7. A method as claimed in claim 1 wherein the compound of formula (I) is as defined in claim 1, wherein R$_1$ is hydrogen and R$_2$ is propionate.

8. A method as claimed in claim 1 wherein the compound of formula (I) is as defined in claim 1, wherein R$_1$ is hydrogen and R$_2$ is butyrate.

9. A method as claimed in claim 5 wherein the active ingredient is present in an amount of 0.2-0.8% by weight.

\* \* \* \* \*

UNITED STATES PATENT AND TRADEMARK OFFICE
CERTIFICATE OF CORRECTION

PATENT NO. : 8,143,240 B2
APPLICATION NO. : 12/457870
DATED : March 27, 2012
INVENTOR(S) : Ajani et al.

It is certified that error appears in the above-identified patent and that said Letters Patent is hereby corrected as shown below:

On the title page

Item (57), Abstract, "17α,21-Dihydroxypregna-4,9-diene-3,20-dione" should read
--17α,21-Dihydroxypregna-4,9(11)-diene-3,20-dione--.

In the specification

Column 1
Lines 27-28, "21-hydroxypregna-4,9-diene-3,20-dione-17α-butyrate" should read
--21-hydroxy-pregna-4,9(11)-diene-3,20-dione-17α-butyrate--.

Column 1
Line 57, "21-hydroxy-pregna-4,9-diene-3,20-dione-17α-butanoate" should read
--21-hydroxy-pregna-4,9(11)-diene-3,20-dione-17α-butanoate--.

Column 1
Lines 64-65, "17α,21-dihydroxypregna-4,9-diene-3,20-dione" should read
--17α,21-dihydroxypregna-4,9(11)-diene-3,20-dione--.

Column 3
Line 8, "17α,21-dibutanoyl-pregna-4,9-diene-3,20-dione" should read
--17α,21-dibutanoyloxy-pregna-4,9(11)-diene-3,20-dione--.

Column 3
Line 9, "17α-hydroxy-21-butanoyl-pregna-4,9-diene-3,20-dione" should read
--17α-hydroxy-21-butanoyloxy-pregna-4,9(11)-diene-3,20-dione--.

Column 3
Line 10, remove "17α-hydroxy-21-butanoyl-pregna-49-di-ene-3,20-dione".

Signed and Sealed this
Twenty-eighth Day of June, 2016

Michelle K. Lee
*Director of the United States Patent and Trademark Office*

In the specification

Column 3
Line 11, "17α-butanoyl-21-octadecanoyl-pregna-4,9-diene-3,20-dione" should read
--17α-butanoyloxy-21-octadecanoyloxy-pregna-4,9(11)-diene-3,20-dione--.

Column 3
Lines 12-13, "17α-octadecanoyl-21-butanoyl-pregna-4,9-diene-3,20-dione" should read
--17α-octadecanoyloxy-21-butanoyloxy-pregna-4,9(11)-diene-3,20-dione--.

Column 3
Line 34, "skine" should read --skin--.

Column 3
Lines 43-44, "17α-propionyl-21-hydroxy-pregna-4,9-diene-3,20-dione" should read
--17α-propionyloxy-21-hydroxy-pregna-4,9(11)-diene-3,20-dione--.

Column 3
Lines 60-61, "17α,21-dihydroxypregna-4,9-diene-3,20-dione" should read
--17α,21-dihydroxypregna-4,9(11)-diene-3,20-dione--.

Column 4
Line 6, "o" should read --or--.

Column 4
Lines 21-23, "17α-acyl-21-hydroxypregna-4-ene-3,20-dione or 17α-acyl-21-hydroxypregna-4,9-diene-3,20-dione" should read --17α-acyloxy-21-hydroxypregna-4-ene-3,20-dione or 17α-acyloxy-21-hydroxypregna-4,9(11)-diene-3,20-dione--.

Column 4
Line 34, "17α,21-dibutanoyl-pregna-4,9-diene-3,20-dione" should read
--17α,21-dibutanoyloxy-pregna-4,9(11)-diene-3,20-dione--.

Column 4
Lines 36-37, "17α,21-dihydroxypregna-4,9-diene-3,20-dione" should read
--17α,21-dihydroxypregna-4,9(11)-diene-3,20-dione--.

Column 4
Lines 52-53, "17α,21-dibutanoyl-pregna-4,9-diene-3,20-dione" should read
--17α,21-dibutanoyloxy-pregna-4,9(11)-diene-3,20-dione--.

Column 4
Line 56, "17α,21- dibutanoyl-pregna-4-ene-3,20-dione" should read
--17α,21-dibutanoyloxy-pregna-4-ene-3,20-dione--.

In the specification

Column 4
Lines 60-61, "17α-hydroxy-21-butanoyl-pregna-4,9-diene-3,20-dione" should read
--17α-hydroxy-21-butanoyloxy-pregna-4,9(11)-diene-3,20-dione--.

Column 4
Lines 63-64, "17α,21-dihydroxypregna-4,9-diene-3,20-dione" should read
--17α,21-dihydroxypregna-4,9(11)-diene-3,20-dione--.

Column 5
Lines 7-8, "17α-hydroxy-21-butanoyl-pregna-4,9-diene-3,20-dione" should read
--17α-hydroxy-21-butanoyloxy-pregna-4,9(11)-diene-3,20-dione--.

Column 5
Lines 12-13, "17α-hydroxy-21-butanoyl-pregna-4-ene-3,20-dione" should read
--17α-hydroxy-21-butanoyloxy-pregna-4-ene-3,20-dione--.

Column 5
Lines 26-27, "17α-hydroxy-21-butanoyl-pregna-4-ene-3,20-dione" should read
--17α-hydroxy-21-butanoyloxy-pregna-4-ene-3,20-dione--.

Column 5
Lines 32-33, "17α-butanoyl-21-octadecanoyl-pregna-4,9-diene-3,20-dione" should read
--17α-butanoyloxy-21-octadecanoyloxy-pregna-4,9(11)-diene-3,20-dione--.

Column 5
Lines 35-36, "17α,21-dihydroxy-pregna-4,9-diene-3,20-dione" should read
--17α,21-dihydroxy-pregna-4,9(11)-diene-3,20-dione--.

Column 5
Lines 41-42, "17α-butanoyl-21-hydroxy-pregna-4,9-diene-3,20-dione" should read
--17α-butanoyloxy-21-hydroxy-pregna-4,9(11)-diene-3,20-dione--.

Column 5
Lines 53-54, "17α-butanoyl-21-octadecanoyl-pregna-4,9-diene-3,20-dione" should read
--17α-butanoyloxy-21-octadecanoyloxy-pregna-4,9(11)-diene-3,20-dione--.

Column 5
Lines 57-58, "17α-butanoyl-21-octadecanoyl-pregna-4-ene-3,20-dione" should read
--17α-butanoyloxy-21-octadecanoyloxy-pregna-4-ene-3,20-dione--.

Column 5
Lines 63-64, "17α-octadecanoyl-21-butanoyl-pregna-4,9-diene-3,20-dione" should read
--17α-octadecanoyloxy-21-butanoyloxy-pregna-4,9(11)-diene-3,20-dione--.

In the specification

Column 6
Line 1, "17α,21-dihydroxy-pregna-4,9-diene-3,20-dione" should read
--17α,21-dihydroxy-pregna-4,9(11)-diene-3,20-dione--.

Column 6
Lines 9-10, "17α-hydroxy-21-allylcarbonyloxy-pregna-4,9-diene-3,20-dione" should read
--17α-hydroxy-21-allylcarbonyloxy-pregna-4,9(11)-diene-3,20-dione--.

Column 6
Lines 20-21, "17α-octadecanoyl-21-allylcarbonyloxy-pregna-4,9-diene-3,20-dione" should read --17α-octadecanoyloxy-21-allylcarbonyloxy-pregna-4,9(11)-diene-3,20-dione--.

Column 6
Lines 36-37, "17α-octadecanoyl-21-hydroxy-pregna-4-ene-3,20-dione" should read
--17α-octadecanoyloxy-21-hydroxy-pregna-4-ene-3,20-dione--.

Column 6
Lines 45-46, "17α-octadecanoyl-21-butanoyl-pregna-4,9-diene-3,20-dione" should read
--17α-octadecanoyloxy-21-butanoyloxy-pregna-4,9(11)-diene-3,20-dione--.

Column 6
Lines 52-53, "17α-octadecanoyl-21-butanoyl-pregna-4-ene-3,20-dione" should read
--17α-octadecanoyloxy-21-butanoyloxy-pregna-4-ene-3,20-dione--.

Column 6
Line 66, "17α,21-dibutanoyl-pregna-4-ene-3,20-dione" should read
--17α,21-dibutanoyloxy-pregna-4-ene-3,20-dione--.

Column 7
Line 1, "17α-propionyl-21-hydroxy-pregna-4-ene-3,20-dione" should read
--17α-propionyloxy-21-hydroxy-pregna-4-ene-3,20-dione--.

Column 7
Lines 6-7, "17α-propionyl-21-hydroxy-pregna-4,9-diene-3,20-dione" should read
--17α-propionyloxy-21-hydroxy-pregna-4-ene-3,20-dione--.